United States Patent
Yoda et al.

(10) Patent No.: US 10,327,728 B2
(45) Date of Patent: Jun. 25, 2019

(54) X RAY COMPUTED TOMOGRAPHY APPARATUS AND SCAN START TIMING DETERMINATION METHOD

(71) Applicant: Toshiba Medical Systems Corporation, Otawara-shi (JP)

(72) Inventors: Takahiro Yoda, Nasushiobara (JP); Katsuhiko Ishida, Nasushiobara (JP); Masakazu Matsuura, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 703 days.

(21) Appl. No.: 14/949,119

(22) Filed: Nov. 23, 2015

(65) Prior Publication Data

US 2016/0073997 A1 Mar. 17, 2016

Related U.S. Application Data

(63) Continuation of application No. PCT/JP2014/065380, filed on Jun. 10, 2014.

(30) Foreign Application Priority Data

Jun. 11, 2013 (JP) .................. 2013-123095

(51) Int. Cl.
*A61B 6/03* (2006.01)
*A61B 6/00* (2006.01)

(52) U.S. Cl.
CPC .............. *A61B 6/542* (2013.01); *A61B 6/032* (2013.01); *A61B 6/469* (2013.01); *A61B 6/481* (2013.01);

(Continued)

(58) Field of Classification Search
CPC ........... A61B 6/032; A61B 6/481; A61B 6/56; A61B 6/563; A61B 6/54; A61B 6/542
(Continued)

(56) References Cited

U.S. PATENT DOCUMENTS

| 5,594,772 A | * | 1/1997 | Toki ..................... A61B 5/0456 378/114 |
| 6,188,744 B1 | * | 2/2001 | Shinohara .............. A61B 6/032 378/8 |

(Continued)

FOREIGN PATENT DOCUMENTS

| JP | 2000-287965 | 10/2000 |
| JP | 2001-054519 | 2/2001 |

(Continued)

OTHER PUBLICATIONS

International Search Report dated Aug. 12, 2014 in PCT/2014/065380 filed Jun. 10, 2014 (with English translation).

(Continued)

*Primary Examiner* — Allen C. Ho
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, an X-ray detector, a projection data generation circuitry, a setting circuitry, and a scan start timing determination circuitry. The setting circuitry configured to set a region of interest on a slice image generated by a first scan for the object. The scan start timing determination circuitry configured to determine, based on a plurality of projection data values of interest corresponding to the region of interest out of the projection data values generated by a second scan at a dose lower than (Continued)

that in the first scan, a timing of terminating the second scan and starting a third scan at a dose higher than that in the second scan.

10 Claims, 7 Drawing Sheets

(52) U.S. Cl.
CPC .............. *A61B 6/54* (2013.01); *A61B 6/56* (2013.01); *A61B 6/563* (2013.01); *A61B 6/463* (2013.01); *A61B 6/488* (2013.01); *A61B 6/5205* (2013.01)

(58) Field of Classification Search
USPC .......................................... 378/9, 15, 16, 62
See application file for complete search history.

(56) References Cited

U.S. PATENT DOCUMENTS

| | | | | |
|---|---|---|---|---|
| 6,763,082 | B2* | 7/2004 | Ozaki | A61B 6/032 378/15 |
| 6,765,983 | B2* | 7/2004 | Yan | A61B 6/032 378/8 |
| 6,876,720 | B2* | 4/2005 | Tsuyuki | A61B 6/032 378/4 |
| 7,054,406 | B2* | 5/2006 | Ikeda | A61B 6/032 378/4 |
| 7,085,343 | B2* | 8/2006 | Shinno | A61B 6/032 378/19 |
| 7,113,569 | B2* | 9/2006 | Okumura | A61B 6/032 378/150 |
| 7,145,982 | B2* | 12/2006 | Ikeda | A61B 6/032 378/16 |
| 7,400,755 | B2* | 7/2008 | West | A61N 5/103 382/128 |
| 7,630,472 | B2* | 12/2009 | Tsuyuki | A61B 6/541 378/4 |
| 7,653,224 | B2* | 1/2010 | Goto | G06T 11/006 382/128 |
| 7,684,600 | B2* | 3/2010 | Wang | A61B 6/032 382/128 |
| 7,715,519 | B2* | 5/2010 | Tsukagoshi | A61B 6/032 378/4 |
| 7,715,520 | B2* | 5/2010 | Nagata | A61B 6/032 378/16 |
| 7,774,041 | B2* | 8/2010 | Nambu | A61B 6/463 378/19 |
| 7,813,471 | B2* | 10/2010 | Hirokawa | A61B 6/032 378/4 |
| 7,907,772 | B2* | 3/2011 | Wang | A61N 5/103 382/128 |
| 7,912,175 | B2* | 3/2011 | Iisaku | A61B 6/032 378/51 |
| 8,126,109 | B2* | 2/2012 | Tsukagoshi | A61B 6/032 378/51 |
| 8,126,227 | B2* | 2/2012 | Fujisawa | A61B 6/032 128/922 |
| 8,254,656 | B2* | 8/2012 | Ingerman | G01N 23/046 378/4 |
| 8,315,449 | B2* | 11/2012 | Kemper | G06K 9/6223 382/128 |
| 8,428,694 | B2* | 4/2013 | Kalafut | A61B 6/507 382/128 |
| 8,483,799 | B2* | 7/2013 | Böing | A61B 6/032 378/15 |
| 8,538,506 | B2* | 9/2013 | Haras | A61B 6/481 600/407 |
| 8,634,622 | B2* | 1/2014 | Woods | G06K 9/3233 382/131 |
| 8,693,757 | B2* | 4/2014 | Gündel | A61B 6/484 382/131 |
| 8,699,768 | B2* | 4/2014 | Vik | A61B 6/032 378/4 |
| 8,731,252 | B2* | 5/2014 | Arakita | A61B 6/032 382/128 |
| 8,761,339 | B2* | 6/2014 | Tsuyuki | A61B 6/032 378/95 |
| 8,798,227 | B2* | 8/2014 | Tsukagoshi | G06T 11/008 378/4 |
| 8,971,607 | B2* | 3/2015 | Goto | G06T 11/003 382/131 |
| 9,002,089 | B2* | 4/2015 | Grass | G06T 7/32 382/131 |
| 9,047,702 | B2* | 6/2015 | Schmitt | A61B 6/032 |
| 9,050,055 | B2* | 6/2015 | Korporaal | A61B 6/481 |
| 9,084,541 | B2* | 7/2015 | Hiraoka | A61B 6/541 |
| 9,198,625 | B2* | 12/2015 | Tsukagoshi | A61B 6/032 |
| 9,251,560 | B2* | 2/2016 | Ishii | A61B 6/032 |
| 9,561,011 | B2* | 2/2017 | Arakita | A61B 6/504 |
| 9,629,596 | B2* | 4/2017 | Taguchi | A61B 6/032 |
| 9,715,745 | B2* | 7/2017 | Kohara | G06T 5/002 |
| 9,757,075 | B2* | 9/2017 | Mukumoto | A61B 6/03 |
| 9,924,910 | B2* | 3/2018 | Klahr | A61B 6/032 |
| 9,959,389 | B2* | 5/2018 | Kalafut | A61B 6/507 |
| 10,130,320 | B2* | 11/2018 | Saito | A61B 6/032 |
| 2013/0279783 | A1 | 10/2013 | Schmitt et al. | |

FOREIGN PATENT DOCUMENTS

| | | |
|---|---|---|
| JP | 2004-113779 | 4/2004 |
| JP | 2005-253841 | 9/2005 |
| JP | 2006-255241 | 9/2006 |
| JP | 2009-119111 | 6/2009 |
| JP | 2010-178909 | 8/2010 |
| JP | 2011-172819 | 9/2011 |
| WO | WO 2012/093364 A1 | 7/2012 |

OTHER PUBLICATIONS

Written Opinion dated Aug. 12, 2014 in PCT/2014/065380 filed Jun. 10, 2014.

* cited by examiner

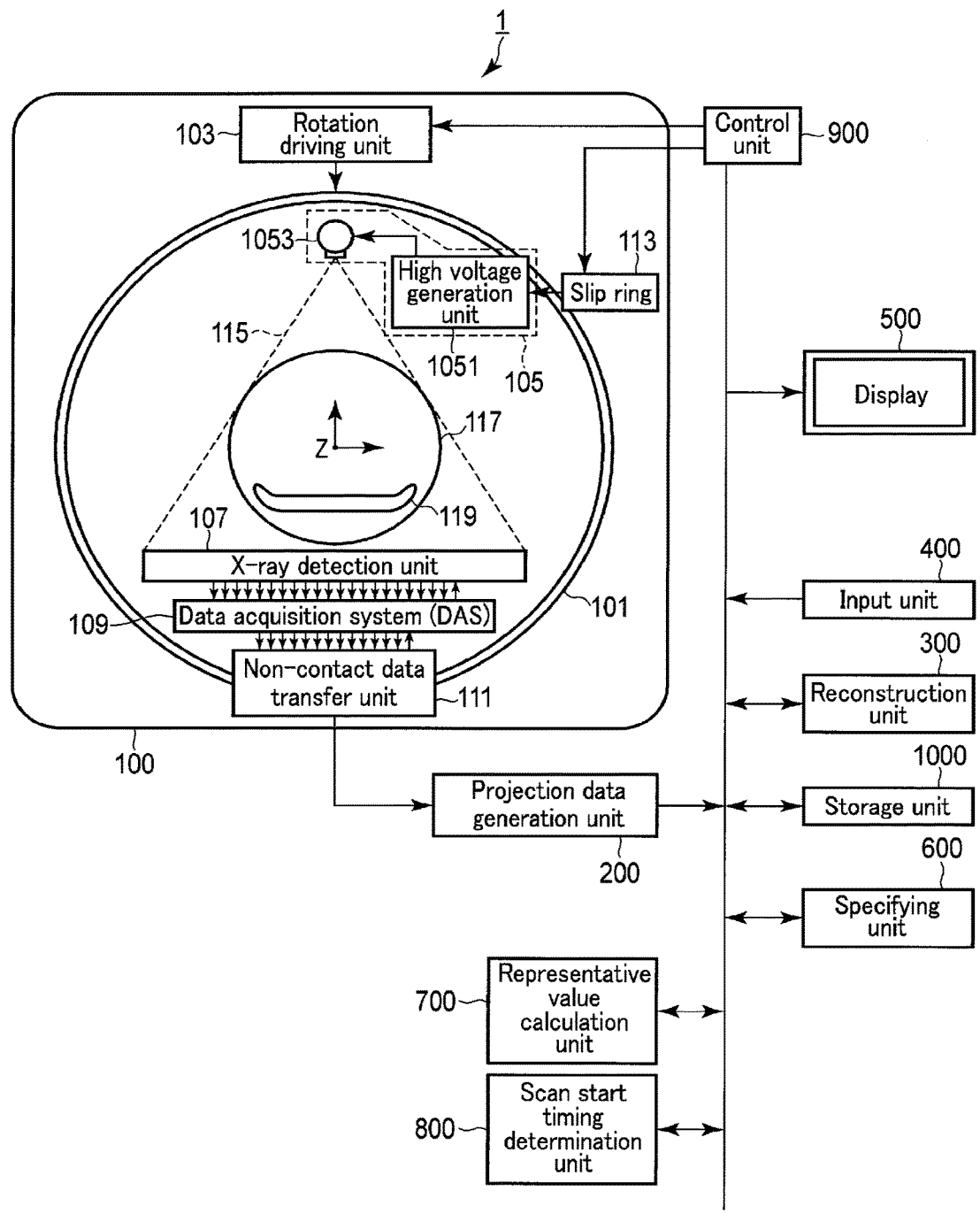
F I G. 1

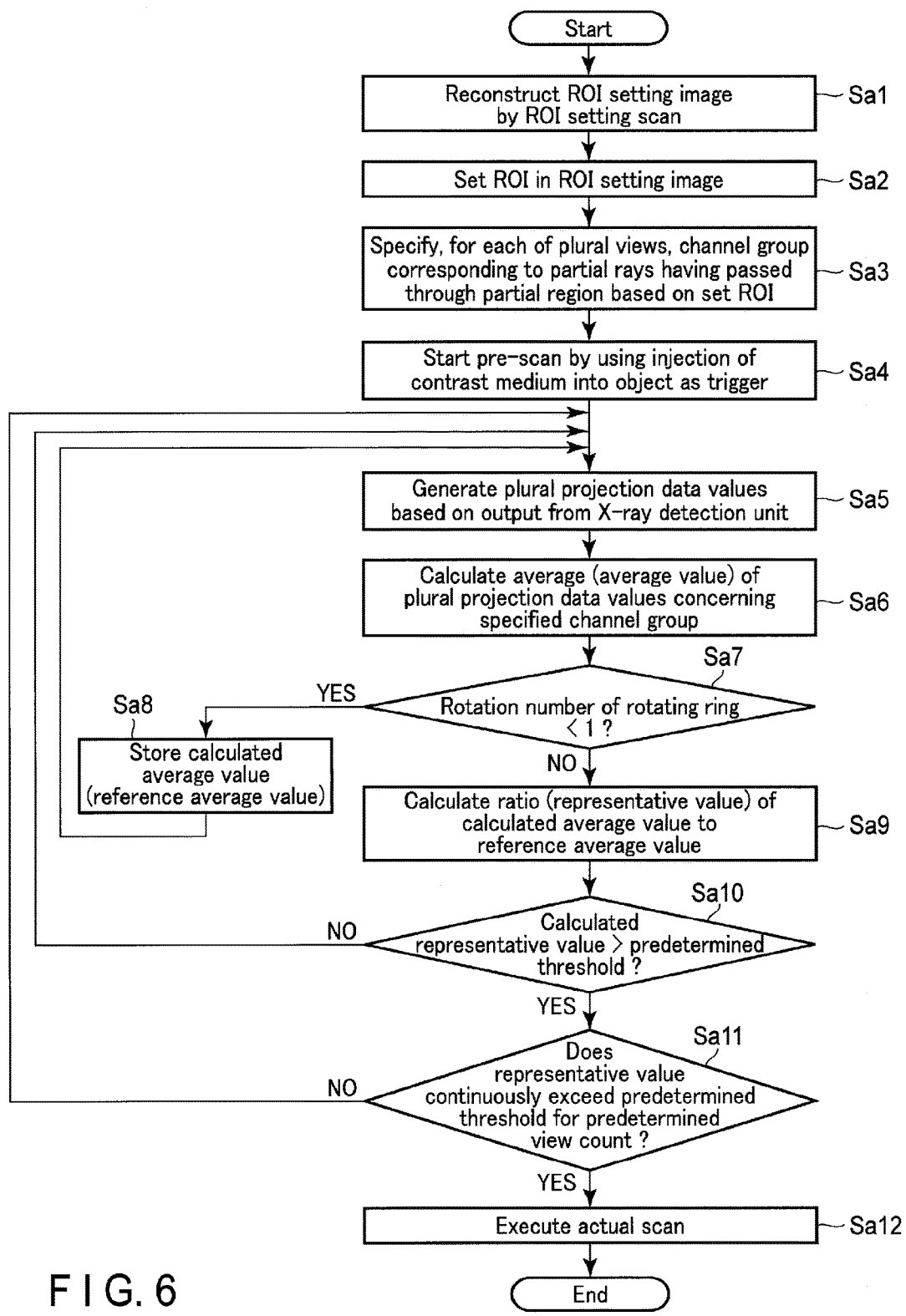
F I G. 6

X RAY COMPUTED TOMOGRAPHY APPARATUS AND SCAN START TIMING DETERMINATION METHOD

CROSS-REFERENCE TO RELATED APPLICATIONS

This application is a Continuation Application of PCT Application No. PCT/JP2014/065380, filed Jun. 10, 2014 and based upon and claiming the benefit of priority from Japanese Patent Application No. 2013-123095, filed Jun. 11, 2013, the entire contents of all of which are incorporated herein by reference.

FIELD

Embodiments described herein relate generally to an X-ray computed tomography apparatus having a contrast medium injection monitoring mechanism, and a scan start timing determination method for the contrast medium injection monitoring mechanism.

BACKGROUND

Conventionally, an X-ray computed tomography (to be referred to as CT hereinafter) apparatus having a contrast medium injection monitoring mechanism monitors a CT value within an area arbitrarily designated on a displayed slice image. The X-ray computed tomography apparatus then starts a next scan (to be referred to as an actual scan) when the CT value being monitored exceeds a predetermined threshold. This can execute the actual scan in synchronism with an inflow of a contrast medium into the designated area.

However, a technique for the contrast medium injection monitoring mechanism imposes the following problems. That is, since it takes time to acquire projection data by one rotation of an X-ray tube around an object and it also takes time to reconstruct an image based on the acquired projection data, determination of an inflow of a contrast medium into an area is delayed. In addition, determination of an inflow of a contrast medium in the contrast medium injection monitoring mechanism is readily influenced by noise and artifacts in the reconstructed image.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing an example of the arrangement of an X-ray computed tomography apparatus according to an embodiment.

FIG. 6 is a flowchart illustrating an example of the procedure of scan start timing determination processing according to the embodiment.

DETAILED DESCRIPTION

Figure 2:
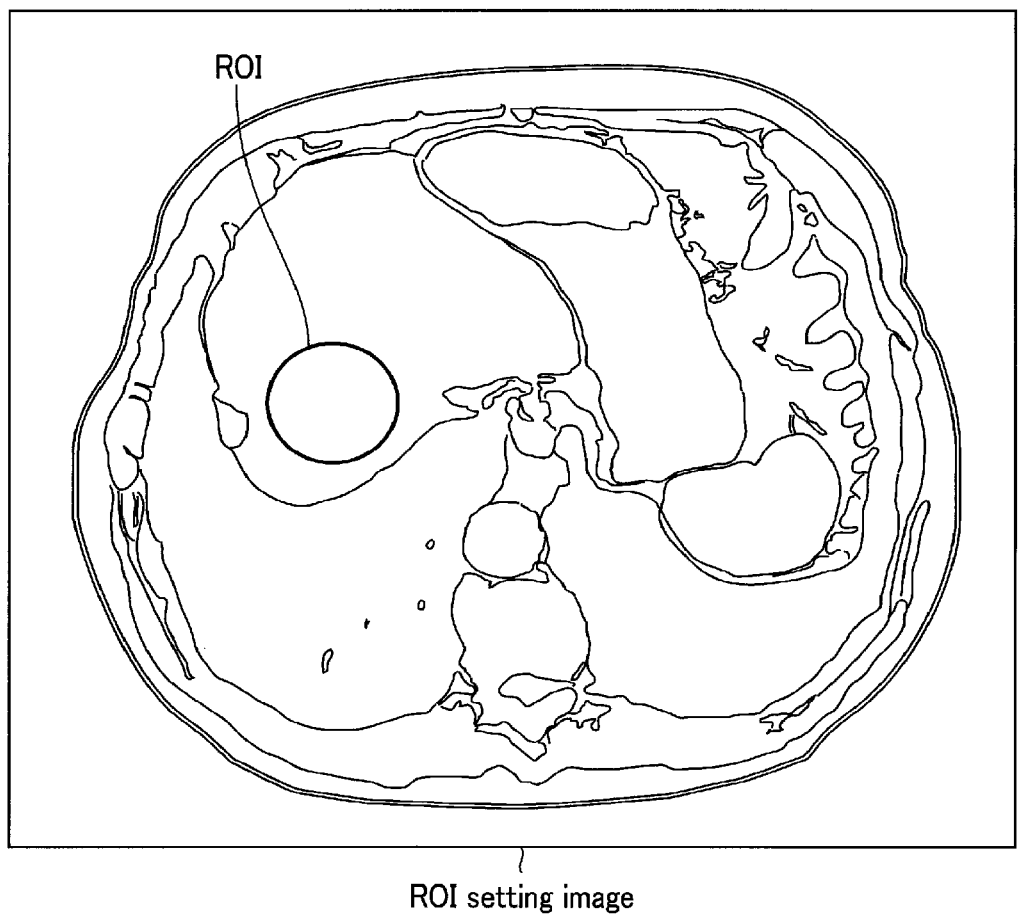
FIG. 2 is a is a view showing examples of a displayed ROI setting image and an ROI set in the ROI setting image according to the embodiment.

In general, according to one embodiment, an X-ray computed tomography apparatus includes an X-ray tube, an X-ray detector, a projection data generation circuitry, a setting circuitry, and a scan start timing determination circuitry. The X-ray tube configured to generate X-rays. The X-ray detector configured to detect X-rays generated from the X-ray generation circuitry and having passed through an object. The projection data generation circuitry configured to generate a plurality of projection data values respectively corresponding to a plurality of channels in the X-ray detection unit based on an output from the X-ray detection circuitry. The setting circuitry configured to set a region of interest on a slice image generated by a first scan for the object. The scan start timing determination circuitry configured to determine, based on a plurality of projection data values of interest corresponding to the region of interest out of the projection data values generated by a second scan at a dose lower than that in the first scan, a timing of terminating the second scan and starting a third scan at a dose higher than that in the second scan.

An embodiment of an X-ray computed tomography apparatus (to also be referred to as an X-ray CT apparatus hereinafter) will be described below with reference to the accompanying drawings. Note that there are provided various types of X-ray computed tomography apparatuses including a rotate/rotate-type apparatus in which an X-ray generation unit and an X-ray detection unit integrally rotate around an object, and a stationary/rotate-type apparatus in which a number of X-ray detection elements arrayed in a ring are fixed and only an X-ray generation unit rotates around an object. Any type is applicable to this embodiment. In addition, in order to reconstruct an image, projection data corresponding to one rotation around an object, that is, 360° is required, or (180°+fan angle) projection data is required even in the half scan method. Either reconstruction scheme is applicable to this embodiment.

As mechanisms of changing incident X-rays into charges, the following techniques are the mainstream: an indirect conversion type that converts X-rays into light through a phosphor such as a scintillator and converts the light into charges through photoelectric conversion elements such as photodiodes, and a direct conversion type that uses generation of electron hole pairs in a semiconductor such as selenium by X-rays and migration of the electron hole pairs to an electrode, that is, a photoconductive phenomenon. As an X-ray detection element, either of these schemes can be adopted.

Furthermore, in recent years, with advances toward the commercialization of a so-called multi-tube type X-ray computed tomography apparatus having a plurality of pairs of X-ray generation units and X-ray detection units mounted on a rotating ring, related techniques have been developed. This embodiment is applicable to both a conventional single-tube type X-ray computed tomography apparatus and a multi-tube type X-ray computed tomography apparatus. When using the multi-tube type X-ray computed tomography apparatus, a plurality of tube voltages respectively applied to a plurality of tubes are different (multi-tube scheme). The single-tube type X-ray computed tomography apparatus will be exemplified here. In addition, each X-ray detection element may be a two-layer detection element having a front-surface detection portion that detects low-energy X-rays and a rear-surface detection portion that is provided on the rear surface of the front-surface detector to detect high-energy X-rays. For the sake of simplicity, assume that the X-ray detection unit uses one-layer X-ray detection elements.

Note that the same reference numerals in the following description denote constituent elements having almost the same functions and arrangements, and a repetitive description will be made only when required.

FIG. 1 shows the arrangement of an X-ray computed tomography apparatus 1 according to this embodiment. The X-ray computed tomography apparatus 1 includes a gantry unit 100, a projection data generation unit 200, a reconstruction unit 300, an input unit 400, a display unit 500, a specifying unit 600, a representative value calculation unit 700, a scan start timing determination unit 800, a control unit 900, and a storage unit 1000. Note that the X-ray computed tomography apparatus 1 may include an interface (to be referred to as an I/F hereinafter) (not shown). The I/F connects the X-ray computed tomography apparatus 1 to an electronic communication line (to be referred to as a network hereinafter). A radiology department information management system (not shown), a hospital information system (not shown), and the like are connected to the network.

The gantry unit 100 accommodates a rotating support mechanism (not shown). The rotating support mechanism includes a rotating ring 101, a ring support mechanism that supports the rotating ring 101 to be rotatable about a rotation axis Z, and a rotation driving unit (electric motor) 103 that drives the rotation of the rotating ring 101. The rotating ring 101 incorporates an X ray generation unit 105, a collimator unit (not shown), an area detector (to be referred to as an X ray detection unit hereinafter) 107 also called a two dimensional array type or multi row type, a data acquisition system (to be referred to as a DAS hereinafter) 109, a non-contact data transfer unit 111, a cooling device (not shown), a gantry control device (not shown), and the like.

The X-ray generation unit 105 includes a high voltage generation unit 1051 and an X-ray tube 1053. The high voltage generation unit 1051 generates a tube voltage to be applied to the X-ray tube 1053 and a tube current to be supplied to the X-ray tube 1053 by using power supplied via a slip ring 113 under the control of the control unit 900 (to be described later).

Upon receiving the tube voltage applied from the high voltage generation unit 1051 and the tube current supplied from it, the X-ray tube 1053 emits X-rays from the X-ray focus. If the high voltage generation unit 1051 supplies different tube currents, the X-ray tube 1053 generates X-rays having an energy spectra with different relative intensity respectively corresponding to the plurality of tube currents. For the sake of simplicity, assume that there are two kinds of tube currents including a tube current for an actual scan (to be referred to as an actual scan tube current hereinafter) and a tube current for a pre-scan (to be referred to as a pre-scan tube current hereinafter). The pre-scan tube current is smaller than the actual scan tube current. Therefore, the dose of X-rays generated by the pre-scan tube current is lower than the dose of X-rays generated by the actual scan tube current. The actual scan and pre-scan will be described in detail later in conjunction with the input unit 400.

The collimator unit attached to the X-ray radiation window of the X-ray tube 1053 shapes the X-rays emitted from the X-ray focus into, for example, a cone beam shape (pyramidal shape). An X-ray radiation range is indicated by dotted lines 115. The X-axis is a straight line that is perpendicular to the rotation axis Z and passes through the focus of the emitted X-rays. The Y-axis is a straight line perpendicular to the X-axis and the rotation axis Z. Note that the XYZ coordinate system will be explained as a rotating coordinate system that rotates about the rotation axis Z for the sake of descriptive convenience.

The X-ray detection unit 107 is mounted on the rotating ring 101 at a position and an angle so as to face the X-ray tube 1053 through the rotation axis Z. The X-ray detection unit 107 includes a plurality of X-ray detection elements. In this case, assume that one X-ray detection element forms one channel. A plurality of channels are arrayed two-dimensionally in the Z direction (slice direction) and an arc direction (channel direction) indicated by an arc that is perpendicular to the rotation axis Z, is centered on the focus of the emitted X-rays, and has, as its radius, the distance from that center to the light receiving unit center of an X-ray detection element for one channel.

Note that the X-ray detection unit 107 may be formed from a plurality of modules each having one array of a plurality of X-ray detection elements. In this case, the plurality of modules are arrayed one-dimensionally in almost the arc direction along the channel direction. The plurality of X-ray detection elements may be arrayed two-dimensionally in the two directions: the channel direction and the slice direction. That is, the two-dimensional array is formed by arraying, in the slice direction, a plurality of arrays each including a plurality of channels arrayed one-dimensionally along the channel direction. The X-ray detection unit 107 including the two-dimensional X-ray detection element array may be formed by arraying, in the slice direction, a plurality of arrays each including the plurality of modules arrayed one-dimensionally in almost the arc direction.

When performing imaging or a scan, a top 119 on which an object P is placed is inserted to a cylindrical imaging region 117 between the X-ray tube 1053 and the X-ray detection unit 107. The DAS 109 is connected to the output side of the X-ray detection unit 107.

The DAS 109 is attached, for each channel, with an I-V converter that converts a current signal from each of the plurality of channels of the X-ray detection unit 107 into a voltage, an integrator that periodically integrates these voltage signals in synchronism with an X-ray irradiation period, an amplifier that amplifies an output signal from the integrator, and an analog/digital converter that converts an output signal from the amplifier into a digital signal. Data (pure raw data) output from the DAS 109 is transmitted to the projection data generation unit 200 (to be described later) via the non-contact data transfer unit 111 using magnetic transmission/reception or optical transmission/reception.

The projection data generation unit 200 generates a plurality of projection data values respectively corresponding to the plurality of channels of the X-ray detection unit 107 based on an output from the X-ray detection unit 107. More specifically, the projection data generation unit 200 performs preprocessing for the pure raw data output from the DAS 109. The preprocessing includes, for example, sensitivity nonuniformity correction processing between channels, and processing of correcting an extreme decrease in signal intensity or signal dropout caused by an X-ray strong absorber, mainly a metal portion. The data (called raw data or projection data; projection data in this case) output from the projection data generation unit 200 immediately before reconstruction processing is output to the representative value calculation unit 700 (to be described later) in association with data representing view angles and channel numbers at the time of data acquisition. Note that the projection data may be stored in the storage unit 1000 including a magnetic disk, magnetooptical disk, or semiconductor memory.

Note that the projection data indicates a set of data values (to be referred to as projection data values hereinafter) each corresponding to the intensity of X-rays having passed through the object. For the sake of descriptive convenience, a set of projection data values throughout a plurality of channels which are almost simultaneously acquired by one shot at the same view angle will be referred to as a projection data set. View angles are obtained by representing, by angles in the range of 0° to 360°, the respective positions on a circular orbit obtained when the X-ray tube 1053 revolves about the rotation axis Z, with the angle of the uppermost portion on the circular orbit in an upward vertical direction from the rotation axis Z being 0°. Note that a projection data value of a projection data set which corresponds to each channel is identified by a view angle, cone angle, and channel number.

The reconstruction unit 300 has a function of reconstructing a nearly cylindrical three-dimensional image by the Feldkamp method or the cone beam reconstruction method based on a projection data set acquired at view angles in the range of 360° or (180°+fan angle). The reconstruction unit 300 also has a function of reconstructing a two-dimensional image (tomographic image) by, for example, the fan beam reconstruction method (also called the fan beam convolution back projection method) or the filtered back projection method. The Feldkamp method is a reconstruction method to be used when projection rays intersect a reconstruction plane like a cone beam. The Feldkamp method is an approximate image reconstruction method of performing convolution by regarding a projection beam as a fan projection beam on the premise that the cone angle is small, and performing back projection in a scan along a ray. The cone beam reconstruction method is a reconstruction method which corrects projection data in accordance with the angle of a ray relative to a reconstruction plane as a method of suppressing cone angle errors more than the Feldkamp method. The reconstruction unit 300 reconstructs a slice image concerning the object P based on a projection data set. The reconstructed image (a slice image, a three-dimensional image, or the like) is stored in the storage unit 1000.

The input unit 400 loads various instructions, commands, pieces of information, selections, and settings from an operator into the X-ray computed tomography apparatus 1. The loaded various instructions, commands, pieces of information, selections, and settings are output to the control unit 900 (to be described later) and the like. Although not shown, the input unit (setting unit) 400 includes a trackball, switch buttons, a mouse, and a keyboard for, for example, setting a region of interest (to be referred to as an ROI hereinafter).

The input unit 400 inputs the scan position of a region-of-interest setting scan (to be referred to as an ROI setting scan (first scan) hereinafter) (to be described later) to a scanogram generated and displayed by imaging (to be referred to as scanography hereinafter) for determining a scan start position, imaging conditions, and the like for the object. Note that the input unit 400 may input the scan positions of a pre-scan (second scan) and an actual scan (third scan). The input unit 400 can also input a threshold to be used by the scan start timing determination unit 800. The input threshold may be, for example, the rate (%) of rise of a ratio calculated by the representative value calculation unit 700 in the pre-scan.

The ROI setting scan is a scan for reconstructing a slice image (to be referred to as an ROI setting image hereinafter) reconstructed to set a blood vessel or ROI concerning detection of a contrast medium. The pre-scan is a scan that is executed, after the ROI setting scan and before the actual scan, for the object to which the contrast medium has been injected. In the pre-scan, X-rays with a dose lower than that in the ROI setting scan or actual scan are generated. For the sake of simplicity, assume that the pre-scan is executed from a view angle of 0°.

The actual scan is a scan that is executed for the object in accordance with a timing determined by the scan start timing determination unit 800. For the sake of simplicity, assume that the ROI setting scan, pre-scan, and actual scan are executed at the same scan position. Note that the scan position in the actual scan may be different from that in the ROI setting scan and that in the pre-scan.

The input unit (setting unit) 400 inputs (sets) an ROI to the ROI setting image reconstructed in the ROI setting scan, that is, a slice image of the object, in accordance with an operator instruction. The input ROI is output to the specifying unit 600 (to be described later). FIG. 2 is a view showing examples of the ROI setting image displayed on the display unit 500 and the ROI set in the ROT setting image.

The input unit 400 detects the coordinates of a cursor displayed on a display screen, and outputs the detected coordinates to the control unit 900. Note that the input unit 400 may be a touch panel provided to cover the display screen. In this case, the input unit 400 detects touched and instructed coordinates by a coordinate reading principle such as an electromagnetic induction scheme, an electromagnetostrictive scheme, or a pressure sensitive scheme, and outputs the detected coordinates to the control unit 900.

The display unit 500 displays the ROI setting image, and a reconstruction image (to be referred to as an actual scan image hereinafter) reconstructed by the actual scan. The display unit 500 displays conditions set for X-ray computed tomography. The display unit 500 displays, on the ROI setting image, the ROI input via the input unit 400 (to be described later).

Note that the display unit 500 may display a reconstruction image (to be referred to as a pre-scan image hereinafter) reconstructed based on projection data values acquired in the pre-scan. In this case, the display unit 500 displays the ROI setting image before, for example, the start of the pre-scan or injection of the contrast medium into the object. Then, the display unit 500 may display the pre-scan image after the start of the pre-scan or injection of the contrast medium into the object in place of the ROI setting image. Note that the pre-scan image and ROI setting image may be obtained for the same slice.

Based on the ROI set on the ROI setting image, the specifying unit 600 specifies, for each of the plurality of views (more specifically, view angles), a plurality of channels (to be referred to as a channel group hereinafter) respectively corresponding to a plurality of X-rays (to be referred to as partial rays hereinafter) having passed through a partial region of the object, which corresponds to the ROI. The plurality of channels of a channel group correspond to a plurality of channels which the plurality of partial rays having passed through the partial region at each view angle respectively reach.

Figure 3:
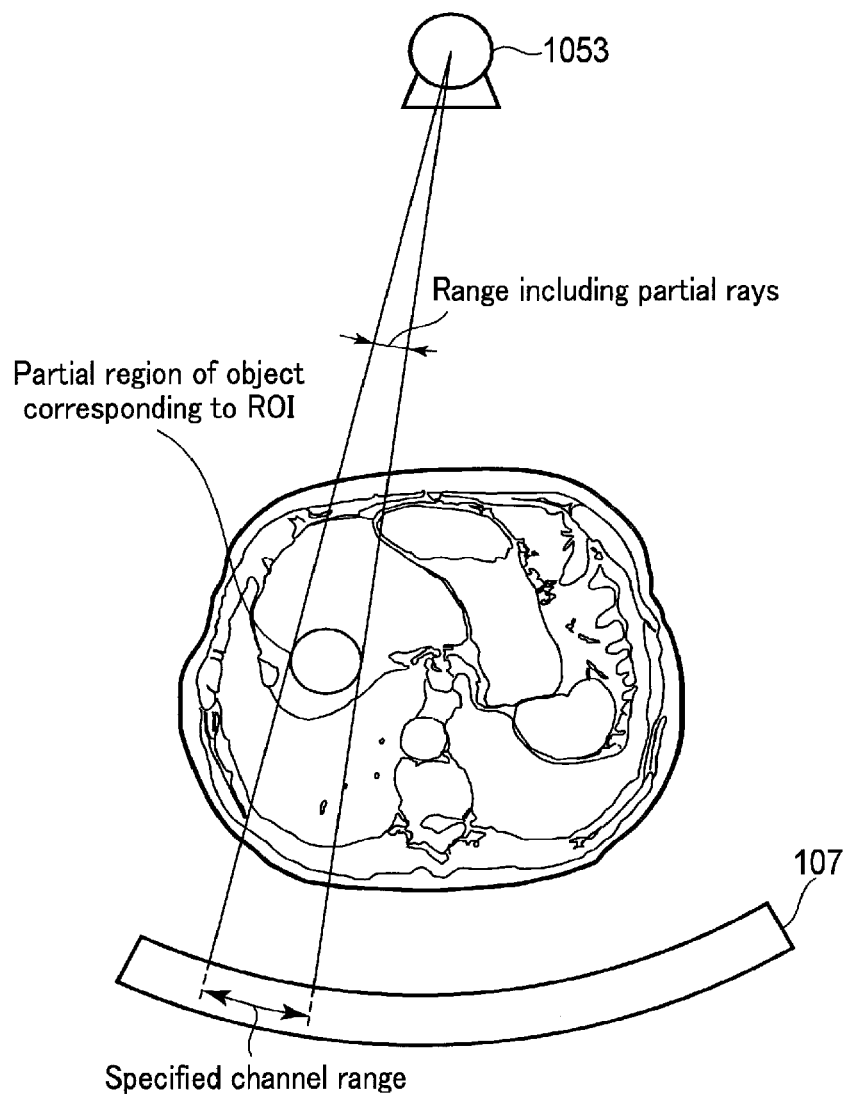
FIG. 3 is a view showing a range including a plurality of partial rays passing through a partial region of an object, which corresponds to the ROI, together with a range including a plurality of specified channels at a given view angle according to the embodiment.

FIG. 3 is a view showing a range including the plurality of partial rays passing through the partial region of the object, which corresponds to the ROI, together with a range (to be referred to as a specified channel range hereinafter) including the plurality of specified channels (channel group). As shown in FIG. 3, the specifying unit 600 specifies the plurality of channels (channel group) included in the specified channel range based on the ROI and the view angle.

For the sake of simplicity, assume that the number of views acquired during one rotation of the X-ray tube 1053 about the rotation axis is 1,200. In this case, an angle between adjacent views of the plurality of views is 360°/1,200=0.3°.

Figure 4:
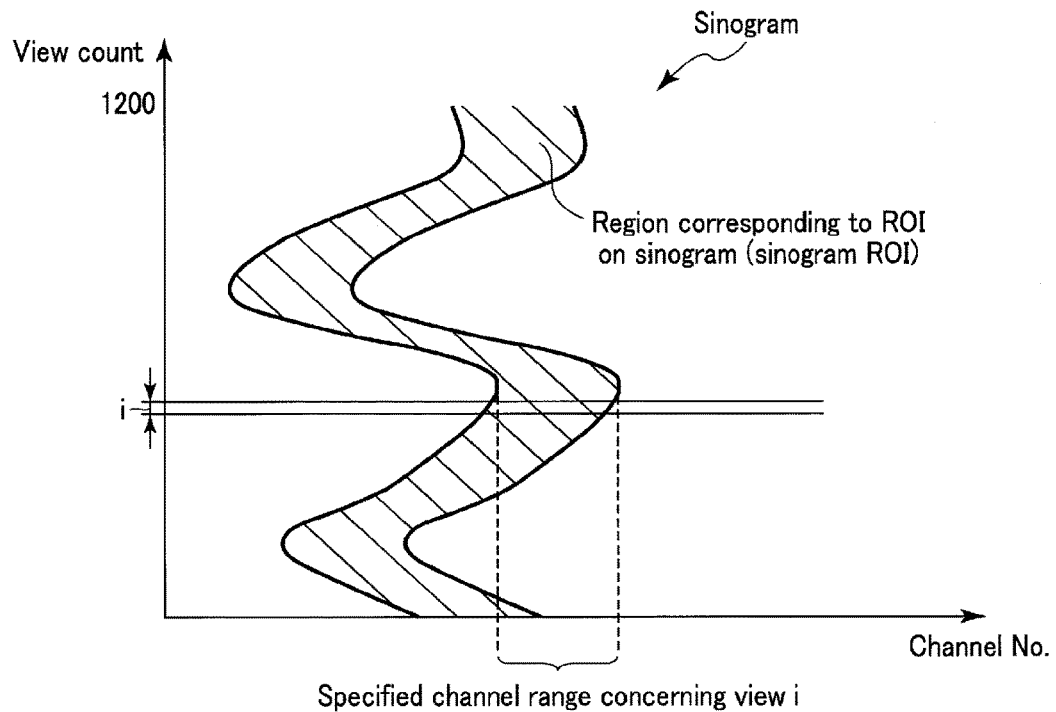
FIG. 4 is a graph showing an example of the distribution of specified channel ranges for 1,200 views in a sinogram that expresses, by oblique lines, projection data values each defined by a view count and a channel number according to the embodiment.

FIG. 4 is a graph showing an example of the distribution (to be referred to as a sinogram ROI hereinafter) of the specified channel ranges for the 1,200 views in a sinogram that expresses, by oblique lines, projection data values each defined by a view count and a channel number. FIG. 4 shows a specified channel range corresponding to a view i on the sinogram ROI.

Note that the specifying unit 600 may specify a plurality of specified channel ranges included in the sinogram ROI for the sinogram based on the view angles and the ROI set in the ROI setting image. The specifying unit 600 outputs a plurality of channel numbers included in the specified channel range corresponding to each of the plurality of views to the representative value calculation unit 700.

The representative value calculation unit 700 calculates a reference value with respect to each view in the pre-scan based on a plurality of projection data values (projection data values of interest) concerning the specified channel range for each view in the pre-scan out of the projection data values related to the pre-scan. The projection data values of interest respectively correspond to the specified channels (channel range) in each view. The representative value calculation unit 700 calculates, for each view, a representative value based on the reference value and projection data values of interest generated in the second scan after the projection data values of interest with respect to the reference value are generated. The representative value is a value representing the plurality of projection data values of interest in the specified channel range.

The representative value calculation unit 700 calculates, as the reference value, the average of the projection data values of interest in each view with respect to a predetermined rotation number of the X-ray generation unit 105 (or the rotating ring 101) in the pre-scan. Note that the representative value calculation unit 700 may calculate, as the reference value, the average of the projection data values of interest in each view before update of the rotation number of the X-ray generation unit 105 in response to update of the rotation number in the pre-scan. The representative value calculation unit 700 calculates, as the representative value, the ratio of the average value of the projection data values of interest to the reference value. Note that the representative value calculation unit 700 may calculate, as the representative value, the difference between the reference value and the average value of the projection data values of interest. Calculation of the reference value and representative value will be described in detail below.

During execution of the pre-scan, the representative value calculation unit 700 calculates the representative value based on the plurality of projection data values respectively corresponding to the plurality of channels included in the specified channel range. More specifically, the representative value calculation unit 700 calculates the average value of the plurality of projection data values (projection data values of interest) with respect to the specified channel range for each view in the pre-scan. That is, the representative value calculation unit 700 calculates a plurality of average values respectively corresponding to the plurality of views by using the plurality of projection data values respectively corresponding to the plurality of channels included in the specified channel range of each view. The representative value calculation unit 700 stores, in the storage unit 1000, the plurality of average values (to be referred to as reference average values (reference values) hereinafter) respectively corresponding to the plurality of views for the first rotation of the rotating ring 101 in the pre-scan.

For the second or subsequent rotation of the rotating ring 101 in the pre-scan, for example, when projection data values are acquired at a view angle of 0°, the representative value calculation unit 700 calculates the average value of the plurality of projection data values within the specified channel range. Furthermore, the representative value calculation unit 700 reads out the reference average value corresponding to a view angle of 0° from the storage unit 1000. The representative value calculation unit 700 calculates the ratio of the calculated average value to the readout reference average value. The representative value calculation unit 700 outputs the calculated ratio to the scan start timing determination unit 800 as the representative value.

When projection data values for a view (a view angle of 0.3°) next to a view at a view angle of 0° are acquired, the representative value calculation unit 700 calculates the average value of the plurality of projection data values within the specified channel range. The representative value calculation unit 700 reads out the reference average value corresponding to a view angle of 0.3° from the storage unit 1000. The representative value calculation unit 700 calculates the ratio of the calculated average value to the readout reference average value. The representative value calculation unit 700 outputs the calculated ratio to the scan start timing determination unit 800 as the representative value.

When projection data values are acquired for each view, the representative value calculation unit 700 repeats the above processing. The representative value calculation unit 700 stops the above processing in synchronism with the end of the pre-scan. Note that the representative value calculation unit 700 may calculate the representative value for the pure raw data output from the DAS 109 in the same manner.

Note that the representative value calculation unit 700 may calculate the difference value between the reference average value and the calculated average value as the representative value for each view. The difference value may be obtained by subtracting the reference average value from the calculated average value or by subtracting the calculated average value from the reference average value. Furthermore, the representative value calculation unit 700 may calculate the absolute value of the difference value as the representative value for each view.

Note that the reference value may be updated, as needed, in correspondence with the rotation number in the pre-scan, as described above. For example, the representative value calculation unit 700 calculates, as the reference value, the average of the projection data values of interest in each of the plurality of views before update of the rotation number of the rotating ring 101 incorporating the X-ray generation unit 105 in response to update of the rotation number in the pre-scan. Then, based on the reference value and projection data values of interest generated in the pre-scan after the projection data values of interest with respect to the reference value are generated, the representative value calculation unit 700 calculates, for each view, a representative value representing the projection data values of interest in response to generation of the projection data values of interest.

Based on the plurality of projection data values of interest corresponding to the region of interest out of the projection data values generated in the pre-scan at a dose lower than that in the ROT setting scan, the scan start timing determination unit 800 terminates the pre-scan, and determines a timing at which the actual scan at a dose higher than that in the pre-scan starts. For example, in response to the fact that the representative value continuously exceeds a predetermined threshold for a predetermined view count, the scan start timing determination unit 800 determines an actual scan start timing. Determination of an actual scan start timing will be described in detail below.

The scan start timing determination unit 800 stores the predetermined threshold and the predetermined view count. Note that the predetermined threshold and the predetermined view count may be stored in the storage unit 1000 (to be described later). The scan start timing determination unit 800 compares the representative value output from the representative value calculation unit 700 with the predetermined threshold. The scan start timing determination unit 800 determines, as an actual scan start timing, a point of time at which the representative value calculated for each view exceeds the threshold for the predetermined view count. The scan start timing determination unit 800 outputs the determined actual scan start timing to the control unit 900 (to be described later). Note that the scan start timing determination unit 800 may determine the actual scan start timing by using a view angle instead of the view count. In this case, the scan start timing determination unit 800 stores a predetermined view angle instead of the predetermined view count.

More specifically, the scan start timing determination unit 800 stores a view count corresponding to the representative value exceeding the predetermined threshold. The scan start timing determination unit 800 calculates an addition view count by adding the predetermined view count to the stored view count. The scan start timing determination unit 800 determines whether the representative value calculated for each view continuously exceeds the predetermined threshold from the stored view count to the addition view count. That is, if the representative value continuously exceeds the predetermined threshold up to the addition view count, the scan start timing determination unit 800 determines a point of time corresponding to the addition view count as the actual scan start timing. The predetermined view count is, for example, 100.

Figure 5:
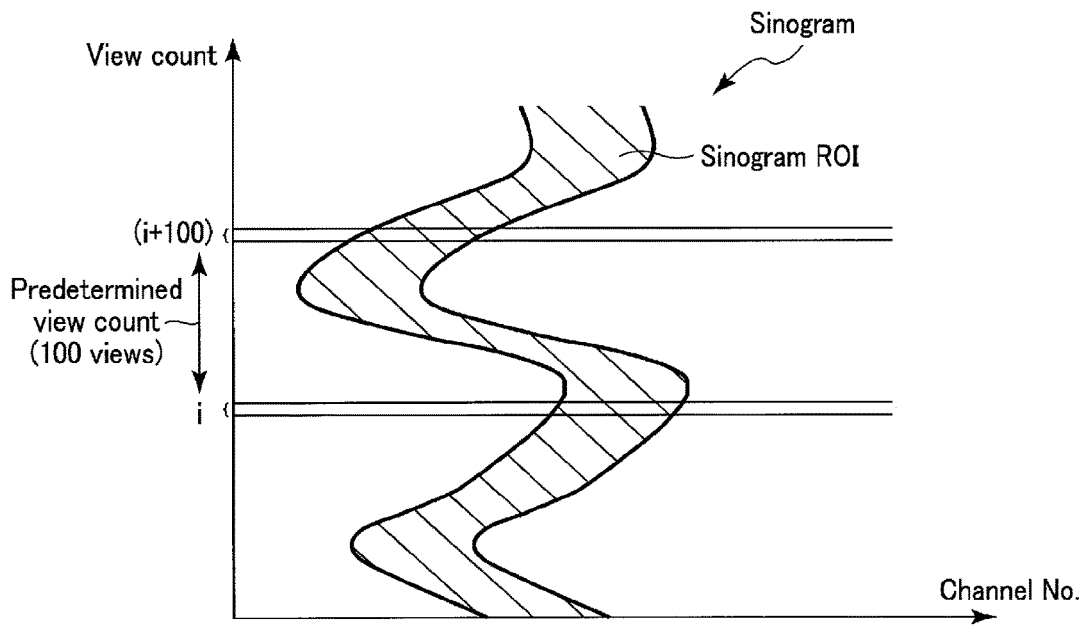
FIG. 5 is a graph for explaining a scan start timing in sinogram data at a given rotation number according to the embodiment.

FIG. 5 is a graph for explaining the scan start timing in sinogram data at a given rotation number. As shown in FIG. 5, at a given view count i, the representative value exceeds the predetermined threshold. If the predetermined view count is, for example, 100, the scan start timing determination unit 800 determines, as the actual scan start timing, a point of time at which the representative value continuously exceeds the predetermined threshold up to a view count (i+100).

In the pre-scan, if the reference value is updated, as needed, in correspondence with the rotation number of the rotating ring 101, after the representative value representing the projection data values of interest exceeds the predetermined threshold, the scan start timing determination unit 800 determines the actual scan start timing in response to the fact that the representative value continuously maintains a predetermined sign (for example, plus) for the predetermined view count.

The control unit 900 functions as the main unit of the X-ray computed tomography apparatus 1. The control unit 900 includes a CPU and a memory (neither of which is shown). The control unit 900 controls the high voltage generation unit 1051, the gantry unit 100, and the like to perform X-ray computed tomography based on examination schedule data and control programs stored in a memory (not shown). More specifically, the control unit 900 temporarily stores operator instructions and the like sent from the input unit 400, the radiology department information management system (not shown), the hospital information system (not shown), and the like in the memory (not shown). The control unit 900 controls the high voltage generation unit 1051, the gantry unit 100, and the like based on these pieces of information temporarily stored in the memory. The control unit 900 reads out control programs for executing predetermined image generation/display processing and the like from the storage unit 1000, and loads them in the memory, thereby executing computation/processing and the like concerning various kinds of processes.

The control unit 900 controls the high voltage generation unit 1051, the projection data generation unit 200, the reconstruction unit 300, and the like to execute scanography for the object. The control unit 900 controls the display unit 500 to display a scanogram of the object generated by scanography. The control unit 900 controls the high voltage generation unit 1051, the projection data generation unit 200, and the reconstruction unit 300 to execute the ROI setting scan. A tube current in the ROI setting scan is the same as the actual scan tube current. The control unit 900 controls the reconstruction unit 300 to reconstruct an ROI setting image based on a plurality of projection data values generated by the ROI setting scan. The control unit 900 controls the display unit 500 to display the reconstructed ROI setting image on the display unit 500.

The control unit 900 controls the high voltage generation unit 1051, the projection data generation unit 200, the reconstruction unit 300, and the like to execute the pre-scan. More specifically, the control unit 900 controls the high voltage generation unit 1051 to generate, in the pre-scan, X-rays corresponding to a dose lower than that in the ROI setting scan and that in the actual scan. A tube current supplied from the high voltage generation unit 1051 in the pre-scan is smaller than that in the ROI setting scan and that in the actual scan. The control unit 900 controls the representative value calculation unit 700 to calculate a representative value in response to acquisition of projection data values in the pre-scan. The control unit 900 controls the scan start timing determination unit 800 to determine an actual scan start timing in response to calculation of the representative value.

The control unit 900 controls the reconstruction unit 300 to reconstruct a pre-scan image of the same slice as that of the ROI setting image based on a plurality of projection data values generated by the pre-scan. The control unit 900 controls the display unit 500 to display the pre-scan image on the display unit 500. The control unit 900 controls the display unit 500 to display the ROI setting image displayed on the display unit 500 in place of the pre-scan image.

Upon input of the actual scan start timing from the scan start timing determination unit 800, the control unit 900 controls the X-ray tube 1053, the high voltage generation unit 1051, the rotation driving unit 103, and the like to stop the pre-scan. Furthermore, the control unit 900 controls the high voltage generation unit 1051, the X-ray tube 1053, the rotation driving unit 103, and the like to execute the actual scan by using input of the actual scan start timing as a trigger. The control unit 900 controls the reconstruction unit 300 to reconstruct an actual scan image based on a plurality of projection data values acquired by the actual scan. The control unit 900 controls the display unit to display the actual scan image on the display unit 500.

The storage unit 1000 stores programs concerning various control operations of the X-ray computed tomography apparatus 1. Note that the storage unit 1000 may store a program of determining an actual scan start timing. Furthermore, the storage unit 1000 stores values concerning the actual scan tube current and pre-scan tube current. The storage unit 1000 stores the plurality of projection data values generated by the projection data generation unit 200. The storage unit 1000 stores the scanogram, the sinogram in the pre-scan, the ROI setting image, the pre-scan image, the actual scan image, the reference average value, and the like. Note that the storage unit 1000 may store the predetermined threshold and the predetermined view count.

(Scan Start Timing Determination Function)

A scan start timing determination function is a function of determining an actual scan start timing based on the representative values calculated for respective views, the predetermined threshold, and the predetermined view count in the per-scan. Processing (to be referred to as scan start timing determination processing hereinafter) complying with the scan start timing determination function will be described below.

FIG. 6 is a flowchart illustrating an example of the procedure of the scan start timing determination processing.

Scanography is executed for the object. Based on a scanogram generated by scanography, the start positions of the ROI setting scan and actual scan, imaging conditions, and the like are input via the input unit 400. At the input position, the ROI setting scan is executed. An ROI setting image is reconstructed based on a plurality of projection data values generated by the ROI setting scan (step Sa1). An ROI is set in the ROI setting image (step Sa2). Based on the set ROI, a channel group corresponding to partial rays having passed through a partial region is specified for each of the plurality of views (step Sa3). The pre-scan is started using injection of the contrast medium into the object as a trigger (step Sa4).

A plurality of projection data values are generated based on an output from the X-ray detection unit 107 (step Sa5). The average (average value) of the plurality of projection data values concerning the specified channel group is calculated (step Sa6). If the rotation number of the rotating ring 101 is smaller than 1 (step Sa7), the calculated average value is stored in the storage unit 1000 as a reference average value (step Sa8). If the rotation number of the rotating ring 101 is equal to or larger than 1 (step Sa7), the ratio (representative value) of the calculated average value to the reference average value is calculated (step Sa9). If the calculated representative value is equal to or smaller than the predetermined threshold (step Sa10), steps Sa5, Sa6, and Sa9 are repeated.

If the calculated representative value exceeds the predetermined threshold (step Sa10), the following processing in step Sa11 is executed. That is, if the representative value does not continuously exceed the predetermined threshold for the predetermined view count (step Sa11), steps Sa5, Sa6, and Sa9 are repeated. If the representative value continuously exceeds the predetermined threshold for the predetermined view count (step Sa11), an actual scan start timing is determined, and the actual scan is executed (step Sa12).

Note that if the reference value is updated, as needed, in correspondence with the rotation number of the rotating ring 101 in the pre-scan, a representative value is calculated by setting, as a reference average value, the average value of the same view at an immediately preceding rotation number in step Sa9. In addition, in step Sa11, it is determined whether the representative value continuously maintains a predetermined sign for the predetermined view count after the representative value exceeds the predetermined threshold.

Modification

The difference from the embodiment is that projection data values generated by the ROI setting scan are used as a reference average value. The components of an X-ray computed tomography apparatus according to the modification are the same as those in the embodiment shown in FIG. 1. Components having functions different from those in the embodiment will be described below.

The representative value calculation unit 700 calculates, as a reference average value, the average of a plurality of projection data values concerning a specified channel group in each of a plurality of views in the ROI setting scan. The representative value calculation unit 700 outputs the reference average value to the scan start timing determination unit 800.

(Scan Start Timing Determination Function)

A scan start timing determination function according to the modification is a function of calculating a reference average value using projection data values generated by the ROI setting scan as a reference average value, and determining an actual scan start timing based on representative values calculated for the respective views, a predetermined threshold, and a predetermined view count.

Figure 7:
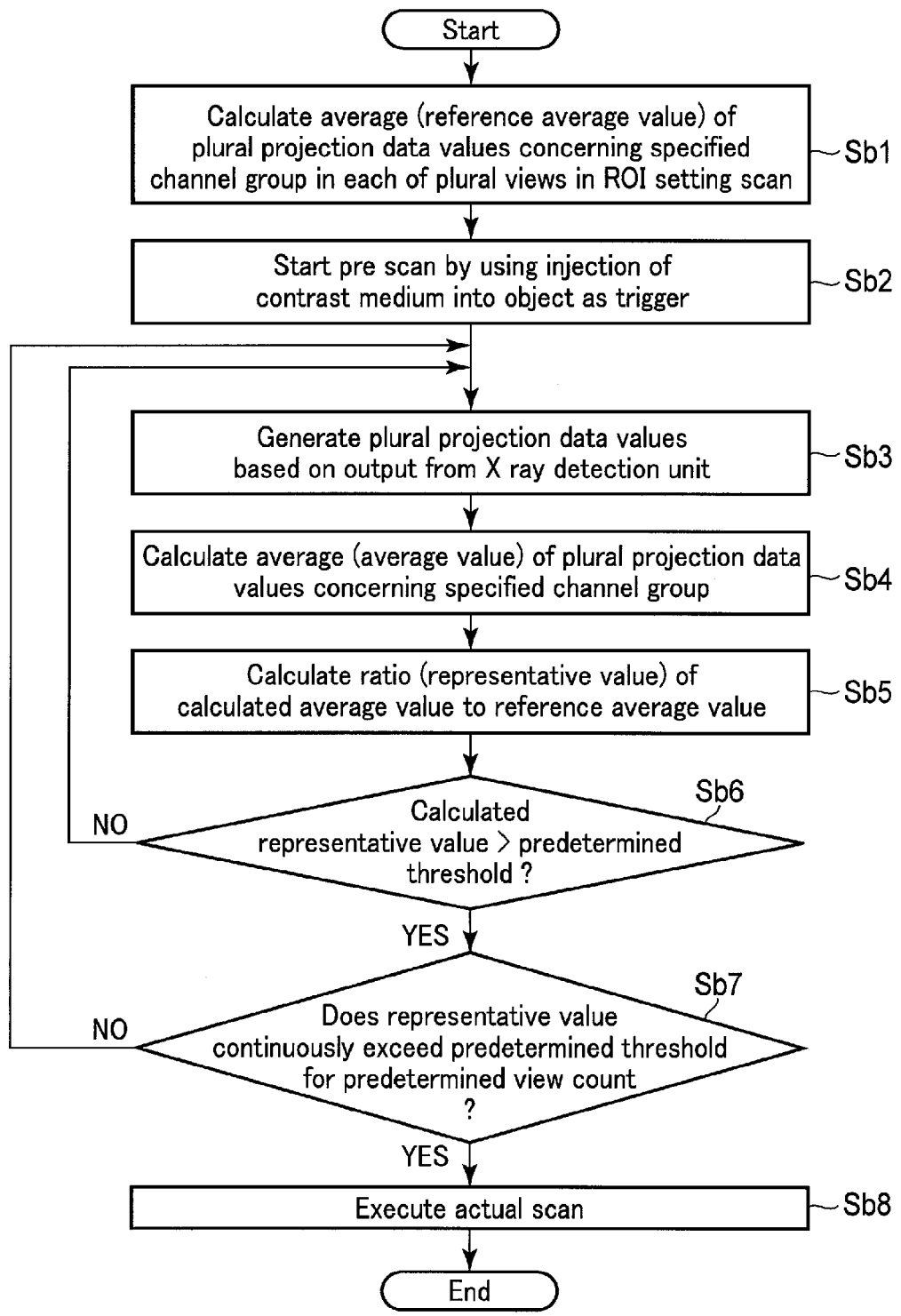
FIG. 7 is a flowchart illustrating an example of the procedure of scan start timing determination processing according to a modification of the embodiment.

FIG. 7 is a flowchart illustrating an example of the procedure of scan start timing determination processing according to the modification.

An ROI setting image is reconstructed based on a plurality of projection data values generated by the ROI setting scan. An ROI is set in the ROI setting image. Based on the set ROI, a channel group corresponding to partial rays having passed through a partial region is specified for each of the plurality of views. In the ROI setting scan, the average (reference average value) of the plurality of projection data values concerning the specified channel group is calculated (step Sb1).

By using injection of the contrast medium into the object as a trigger, the pre-scan is started (step Sb2). A plurality of projection data values are generated based on an output from the X-ray detection unit 107 (step Sb3). The average (average value) of the plurality of projection data values concerning the specified channel group is calculated (step Sb4). The ratio (representative value) of the calculated average value to the reference average value is calculated (step Sb5).

If the calculated representative value is equal to or smaller than the predetermined threshold (step Sb6), steps Sb3 to Sb5 are repeated.

If the calculated representative value exceeds the predetermined threshold (step Sb6), the following processing in step Sb7 is executed. That is, if the representative value does not continuously exceed the predetermined threshold for the predetermined view count (step Sb7), steps Sb3 to Sb6 are repeated. If the representative value continuously exceeds the predetermined threshold for the predetermined view count (step Sb7), an actual scan start timing is determined, and the actual scan is executed (step Sb8).

Note that if the reference value is updated, as needed, in correspondence with the rotation number of the rotating ring 101 in the pre-scan, when the rotation number in the pre-scan is 1, the reference average value of the same view calculated in the ROI setting scan is set as the reference value in step Sb5. On the other hand, if the rotation number in the pre-scan is 2 or more, the reference value in step Sb5 is obtained by calculating a representative value by setting, as a reference average value, the average value of the same view at an immediately preceding rotation number in the pre-scan. In addition, in step Sb7, it is determined whether the representative value continuously maintains a predetermined sign for the predetermined view count after the representative value exceeds the predetermined threshold.

With the aforementioned arrangement, it is possible to obtain the following effects.

The X-ray computed tomography apparatus 1 according to the embodiment can determine an actual scan start timing based on the representative values calculated for the respective views, the predetermined threshold, and the predetermined view count in the pre-scan in which it is determined whether the contrast medium has reached the ROI. More specifically, according to the embodiment, it is possible to specify a channel group corresponding to the preset ROI for each view. That is, according to the embodiment, it is possible to specify a region (sinogram ROI) corresponding to the ROI on a sinogram. According to the embodiment, it is possible to determine an actual scan start timing based on the representative values calculated for the respective views based on the plurality of projection data values concerning the specified channel group, the predetermined threshold, and the predetermined view count. According to the modification of the embodiment, it is possible to calculate a reference average value to be used to calculate a representative value based on a plurality of projection data values in the ROI setting scan before the pre-scan, and the specified channel group.

Consequently, the X-ray computed tomography apparatus 1 according to the embodiment can determine an inflow of the contrast medium into the ROI based on the projection data values acquired for each view. This eliminates the acquisition time taken to acquire projection data by one rotation of the X-ray tube 1053 around the object and the reconstruction time taken to reconstruct an image based on the collected projection data, thereby improving the accuracy of contrast medium injection monitoring. In determination of an inflow of the contrast medium into the ROI, it is possible to nullify the influence of noise and artifacts.

That is, the X-ray computed tomography apparatus 1 according to the embodiment can reduce the influence of organs around the set region of interest on the projection data values of interest by using, as an actual scan start timing determination target, a representative value (ratio or difference) normalized using the reference value. In addition, by starting the actual scan in response to the fact that the representative value continuously exceeds the predetermined threshold for the predetermined view count, it is possible to eliminate the influence of an inflow of the contrast medium into a blood vessel outside the ROI on the representative value.

Figure 8:
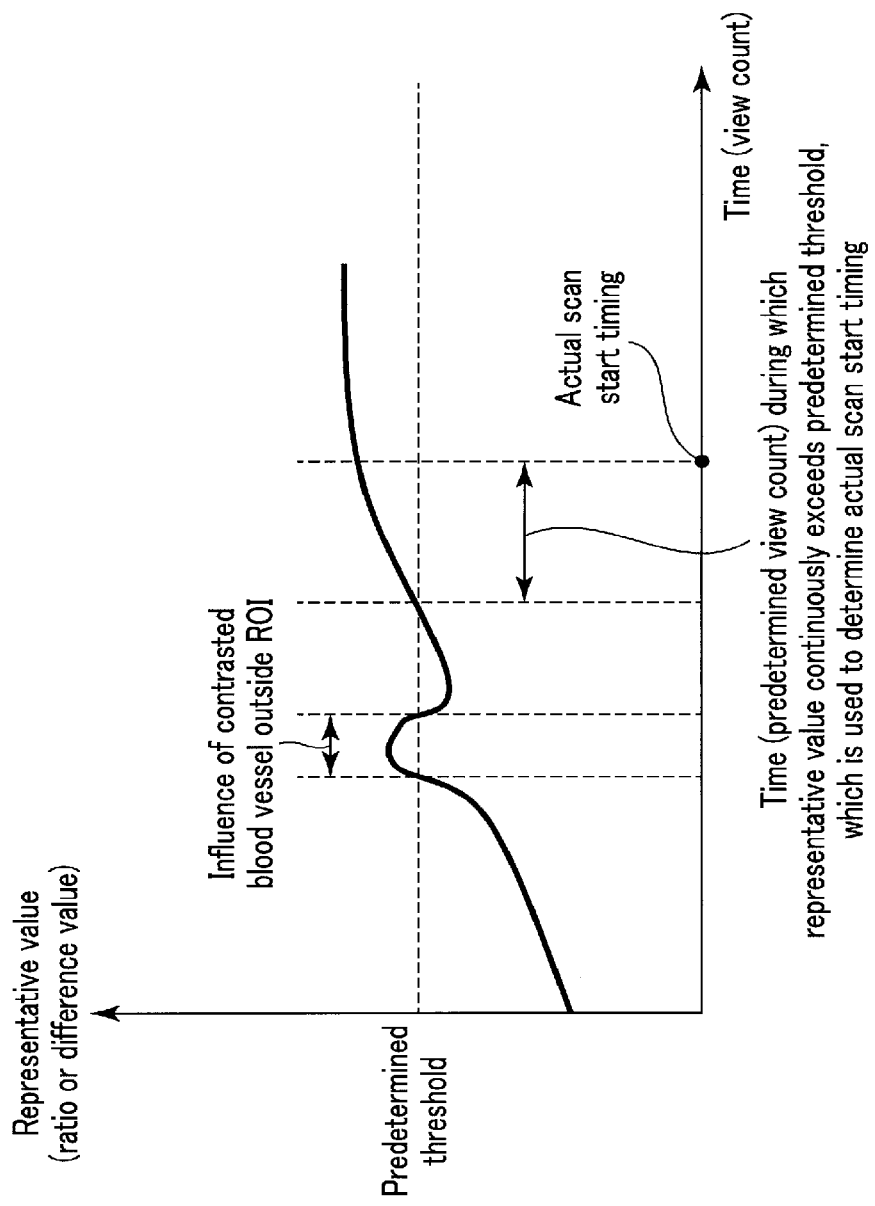
FIG. 8 is a graph showing a temporal change of a representative value in the scan start timing determination processing together with a predetermined threshold and a predetermined view count according to the embodiment.

FIG. 8 shows a temporal change of a representative value in the scan start timing determination processing during the pre-scan together with the predetermined threshold and the predetermined view count. As shown in FIG. 8, the duration of a state in which the representative value exceeds the predetermined threshold is shorter than that corresponding to the predetermined view count due to the influence of a contrasted blood vessel outside the ROI. Therefore, the X-ray computed tomography apparatus 1 according to the embodiment can eliminate the influence of the contrasted blood vessel outside the ROI in the scan start timing determination processing. Consequently, as shown in FIG. 8, the X-ray computed tomography apparatus 1 according to the embodiment can start the actual scan when the period during which the representative value continuously exceeds the predetermined threshold reaches the predetermined view count.

As described above, the X-ray computed tomography apparatus 1 according to the embodiment can improve the accuracy of determination of an inflow of the contrast medium into the ROI in the contrast medium injection monitoring mechanism. It is also possible to reduce the exposure dose of the object.

In addition, the respective functions according to the embodiment can be implemented by installing medical image processing programs for executing the above-described processing in a computer such as a workstation, and loading them in the memory. At this time, the programs capable of causing the computer to execute the above-described method can be distributed by storing the programs in storage media such as magnetic disks (for example, Floppy® disks or hard disks), optical disks (for example, CD-ROMs or DVDs), or semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
   an X-ray tube configured to generate X-rays;
   an X-ray detector configured to detect X-rays generated from the X-ray tube and having passed through an object;
   projection data generation circuitry configured to generate a plurality of projection data values respectively corresponding to a plurality of channels in the X-ray detector based on an output from the X-ray detector;
   setting circuitry configured to set a region of interest on a slice image generated by a first scan for the object; and
   scan start timing determination circuitry configured to determine, based on a plurality of projection data values of interest corresponding to the region of interest of the plurality of projection data values generated by a second scan at a dose lower than a dose in the first scan, a timing of terminating the second scan and starting a third scan at a dose higher than a dose in the second scan.

2. The X-ray computed tomography apparatus of claim 1, wherein the scan start timing determination circuitry determines the timing in response to a representative value representing the plurality of projection data values of interest continuously exceeding a predetermined threshold for a predetermined view count.

3. The X-ray computed tomography apparatus of claim 2, further comprising:
representative value calculation circuitry configured to calculate a reference value concerning each of a plurality of views based on the plurality of projection data values of interest in one of the first scan and the second scan, and calculate, for each view, the representative value based on the reference value and the plurality of projection data values of interest generated in the second scan after the plurality of projection data values of interest with respect to the reference value are generated.

4. The X-ray computed tomography apparatus of claim 3, wherein the representative value calculation circuitry calculates, as the reference value, an average of the plurality of projection data values of interest in each view with respect to a predetermined rotation number of the X-ray tube in one of the first scan and the second scan.

5. The X-ray computed tomography apparatus of claim 4, wherein the representative value calculation circuitry calculates, as the representative value, a ratio of an average value of the plurality of projection data values of interest to the reference value.

6. The X-ray computed tomography apparatus of claim 4, wherein the representative value calculation circuitry calculates, as the representative value, a difference between the reference value and an average value of the plurality of projection data values of interest.

7. The X-ray computed tomography apparatus of claim 1, further comprising:
representative value calculation circuitry configured to calculate, as a reference value, an average of the plurality of projection data values of interest in each of a plurality of views before update of a rotation number of the X-ray tube in response to update of the rotation number in the second scan, and calculate, for each view, a representative value representing the plurality of projection data values of interest based on the reference value and the plurality of projection data values of interest generated in the second scan after the plurality of projection data values of interest with respect to the reference value are generated,
wherein the scan start timing determination circuitry determines the timing in response to the representative value representing the plurality of projection data values of interest continuously maintaining a predetermined sign for a predetermined view count after the representative value exceeds a predetermined threshold.

8. The X-ray computed tomography apparatus of claim 1, further comprising:
specifying circuitry configured to specify, for each of a plurality of views, a plurality of channels respectively corresponding to a plurality of X-rays having passed through a partial region of the object concerning the region of interest,
wherein the plurality of projection data values of interest respectively correspond to the plurality of channels in each view.

9. The X-ray computed tomography apparatus of claim 1, further comprising:
reconstruction circuitry configured to reconstruct the slice image based on the plurality of projection data values concerning the first scan executed before injection of a contrast medium into the object, and reconstruct a reconstruction image of the same slice as that of the slice image based on the plurality of projection data values concerning the second scan executed after the injection of the contrast medium; and
a display configured to display the slice image before the injection of the contrast medium, and display the reconstruction image in place of the slice image after the injection of the contrast medium.

10. A scan start timing determination method comprising:
detecting, with an X-ray detector, X-rays having passed through an object;
generating a plurality of projection data values respectively corresponding to a plurality of channels in the X-ray detector based on an output concerning the detected X-rays;
setting a region of interest on a slice image generated by a first scan for the object; and
determining, based on a plurality of projection data values of interest corresponding to the region of interest out of the projection data values generated by a second scan at a dose lower than that in the first scan, a timing of terminating the second scan and starting a third scan at a dose higher than that in the second scan.

* * * * *